(12) United States Patent  
Buttin et al.

(10) Patent No.: US 11,779,351 B2  
(45) Date of Patent: Oct. 10, 2023

(54) INSTALLATION FOR ROBOTIC SPINE SURGERY

(71) Applicant: SYLORUS ROBOTICS, Saint-Priest (FR)

(72) Inventors: Romain Buttin, Saint Priest (FR); Gautier Daune, Bron (FR); Pierre Roussouly, Saint Cyr au Mont D'or (FR)

(73) Assignee: S.M.A.I.O, Saint-Priest (FR)

( * ) Notice: Subject to any disclaimer, the term of this patent is extended or adjusted under 35 U.S.C. 154(b) by 114 days.

(21) Appl. No.: 17/430,075

(22) PCT Filed: Feb. 13, 2020

(86) PCT No.: PCT/EP2020/053730  
§ 371 (c)(1),  
(2) Date: Aug. 11, 2021

(87) PCT Pub. No.: WO2020/165328  
PCT Pub. Date: Aug. 20, 2020

(65) Prior Publication Data

US 2022/0142657 A1    May 12, 2022

(30) Foreign Application Priority Data

Feb. 14, 2019   (FR) ...................................... 1901512

(51) Int. Cl.  
*A61B 17/16* (2006.01)  
*A61B 34/37* (2016.01)  
(Continued)

(52) U.S. Cl.  
CPC .......... *A61B 17/1671* (2013.01); *A61B 17/17* (2013.01); *A61B 34/37* (2016.02); *A61B 50/13* (2016.02); *A61B 2050/105* (2016.02)

(58) Field of Classification Search  
CPC ..... A61B 17/1671; A61B 34/37; A61B 50/13; A61B 17/17; A61B 2050/105; A61G 13/0054; A61G 13/1225  
See application file for complete search history.

(56) References Cited

U.S. PATENT DOCUMENTS 6,468,265 B1 * 10/2002 Evans .................... A61B 34/35  
606/1  
9,592,096 B2    3/2017 Maillet et al.  
(Continued)

FOREIGN PATENT DOCUMENTS

| EP | 2893898 A1 | 7/2015 |
|---|---|---|
| FR | 2983059 A1 | 5/2013 |
| WO | 2006069288 A2 | 6/2006 |

OTHER PUBLICATIONS

Search Report for French Application No. 1901512 dated Nov. 26, 2019.

(Continued)

*Primary Examiner* — Kevin T Truong  
*Assistant Examiner* — Diana Jones  
(74) *Attorney, Agent, or Firm* — Pearne & Gordon LLP

(57) ABSTRACT

The installation according to the invention has a practical and effective arrangement, comprising an operating table, a robot for posterior spine surgery, as well as a bridge table that comprises, in part, two uprights designed to be separated from the operating table when the installation is in use, while being arranged and rising from the ground on either side of a patient recumbent on the operating table and, in part, a support platform for the robot, this platform resting on the uprights so that, during use, it lies over the patient recumbent on the operating table and being designed, during use, to support the robot extending directly above the spine of the patient recumbent on the operating table.

12 Claims, 4 Drawing Sheets

(51) Int. Cl.
*A61B 50/13* (2016.01)
*A61B 17/17* (2006.01)
*A61B 50/10* (2016.01)

(56) References Cited

U.S. PATENT DOCUMENTS

| | | |
|---|---|---|
| 10,159,534 B2 | 12/2018 | Maillet et al. |
| 10,667,876 B2 | 6/2020 | Maillet et al. |
| 2010/0168562 A1* | 7/2010 | Zhao ................... A61B 34/37 600/426 |
| 2010/0174410 A1* | 7/2010 | Greer ................... A61B 34/37 700/264 |
| 2010/0204713 A1* | 8/2010 | Ruiz Morales .......... B25J 9/041 606/130 |
| 2010/0224022 A1* | 9/2010 | Choi ................... A61B 34/37 901/1 |
| 2015/0196365 A1 | 7/2015 | Kostrzewski et al. |
| 2016/0184032 A1* | 6/2016 | Romo ................... A61B 10/04 901/46 |
| 2016/0235492 A1* | 8/2016 | Morard .............. A61B 17/1757 |
| 2018/0207794 A1* | 7/2018 | Sebring ................... B25J 5/007 |
| 2018/0344421 A1* | 12/2018 | Cagle ................... A61B 50/13 |

OTHER PUBLICATIONS

Search Report for International Application No. PCT/EP2020/053730 dated May 15, 2020.

\* cited by examiner

INSTALLATION FOR ROBOTIC SPINE SURGERY

The present invention relates to an installation for robotic spine surgery.

The surgical treatment of the spine of human patients can lead to placing spinal implants. As such, in order to perform arthrodesis of a segment of several vertebrae, implants are attached to these vertebrae in order to set them together. These implants generally include so-called pedicle screws, to be placed in the pedicles of the vertebrae. The surgical procedures required to place these spinal implants, particularly the pedicle screws, are difficult to perform due to the small size of the bone structures where the implants are to be anchored, the lack of visibility and the criticality of the surrounding anatomical structures, such as the spinal cord, the vena cava, the aorta, etc.

In practice, these surgical procedures are currently performed by orthopedic and neuro-orthopedic surgeons who, after having cleared posterior access to the vertebrae, use ad hoc tools on the latter, in particular bone drilling and screwing tools. To guide their actions and minimize the risk of damaging surrounding anatomical structures, surgeons can work "freehand" using either anatomical landmarks, radiographic sights provided by an image intensifier, or an intraoperative computer navigation system.

For some years now, surgeons can also be assisted by surgical robots that position a guide in relation to the patient's spine to be operated on, into which the surgeon introduces or places a tool that the surgeon manipulates when applying this tool to the spine: this positioning guide is a drilling guide, for example, which is positioned precisely by the robot based on intraoperative data and which is provided with a hole into which the surgeon introduces a drilling tool, it being noted that it is not the robot itself that applies the drilling tool. Examples are provided by US 2015/196365 and FR 2 983 059. Such robotic assistance has real advantages for the precision and repeatability of the surgeon's gestures. However, it suffers from limitations related to the presence of the robot itself in close proximity to the operated patient. Indeed, the robot is typically installed on a dedicated station, which is arranged on one of the lateral edges of the operating table where the patient is recumbent and which can even be attached to this lateral edge of the operating table in a mobile manner. Therefore, the robot and its station occupy a large space on one of the lateral sides of the table, necessarily inducing both a certain discomfort for the surgeons and, more generally, the operating room personnel, and a risk of physical interference with the other operating materials and equipment which are arranged around the table and which are useful for surgical intervention. To limit the size of this station somewhat, at least part of the electronic means of command and control of the robot, including an interface used by the surgeon, can be moved to a remote console placed outside the operating area, but this obliges the surgeon to go back and forth between the patient and this console and thus risks lengthening the duration of the operation. Furthermore, the spine of the operated patient may extend lengthwise asymmetrically in relation to the sagittal plane of the patient, forming more or less pronounced angulations according to a possible asymmetric pathology of the patient: when such an angulation causes the back of the vertebra to be turned to the lateral side of the operating table, opposite to the one where the station supporting the robot is located, the latter may not be able to bring and position the guide on this vertebra, except by moving the station from the lateral side of the operating table to the opposite lateral side of this table, This is particularly difficult during surgery, or unless two robots are installed on stations located on each side of the operating table, which is expensive and increases the problem of space mentioned above.

In a field different from that of spinal surgery, EP 2 893 898 discloses a robotic medical system that is intended for handling catheters and associated materials. This robotic medical system includes an operating table on which a patient can lie. It also includes an archway consisting of two vertical posts and a horizontal beam, which connects the posts above the operating table and supports robotic catheter handling heads. An essential feature of this robotic medical system is that the vertical uprights are mechanically connected to the respective lateral sides of the operating table, in order to hold the arch in position and guide it in translation in relation to the operating table, which makes the system cumbersome and unsuitable for the presence of personnel and equipment that spinal surgery requires.

The purpose of the present invention is to provide a new robotic spine surgery installation with a more convenient and effective arrangement.

To this end, the subject matter of the invention is an installation for robotic spine surgery, comprising:
- an operating table, which is designed to lay a patient thereon,
- a robot for posterior spine surgery, and
- a bridge table comprising:
  - two uprights that are designed to be separated from the operating table when the installation is in use, while being arranged and rising from the ground on either side of the patient recumbent on the operating table, and
  - a platform to support the robot, which rests on the uprights so that, during use, the platform lies over the patient recumbent on the operating table and which is designed, during use, to support the robot extending vertically above the spine of the patient recumbent on the operating table.

One of the ideas behind the invention is to position the surgical robot not laterally to the recumbent patient to be operated on, but above and in alignment with that patient. To this end, the invention provides for the surgical robot to be able to extend vertically above the spine of the recumbent patient, being supported by a platform that overhangs the patient and extends transversely to the latter's spine. This platform is supported by two opposite uprights, which are provided on either side of the recumbent patient and which each extend from the platform to the ground. Thus, this platform and its uprights together form a bridge table that spans the patient: the operating room staff and other operating materials and equipment are not hindered by the robot and by the part of the platform, which overhangs the recumbent patient and supports the robot, while the rest of the bridge table can be dimensioned to have a small footprint and can even advantageously incorporate practical features, such as areas used by the operating room personnel to deposit or store surgical instruments, and/or such as a cabinet where the electronic systems, in particular controllers, useful for the command and control of the installation, in particular the robot, are housed. Moreover, thanks to its arrangement in line with the spine of the patient being operated on, the robot is positioned as close as possible to the vertebrae to be operated on, regardless of the patient, which facilitates the approach of the vertebrae by the robot without the latter having to extend itself according to long and complex kinematics, thus avoiding the need to use "large" robots with very extensive fields of activity, and the robot can work under the same conditions regardless of any left-right asymmetry of the operated spine.

The invention can be implemented with a robot for assisting in surgical procedures, as mentioned above. That being said, the invention finds particularly advantageous application for the case where the robot itself can perform a surgical procedure, such as drilling the pedicles of a vertebra of the operated patient and/or inserting a pedicle screw into these pedicles.

According to additional advantageous features of the installation according to the invention:
- the robot is designed to extend over a field of activity that, when the installation is in use and the bridge table occupies a fixed position alongside the patient recumbent on the operating table, covers several vertebrae of the patient, in particular between three and eight vertebrae of the patient;
- the robot comprises:
  - a foot that is attached to the platform of the bridge table so as, during use, to be substantially centered on the sagittal plane of the patient recumbent on the operating table, and
  - a robotic arm that extends from the foot, being positioned, during use, plumb with the spine of the patient, and which terminates in a spinal surgery effector;
- the bridge table is designed, during use, to position the foot of the robot vertically above the pelvic girdle of the patient recumbent on the operating table;
- the robot is configured, during use, to perform a surgical procedure on the patient recumbent on the operating table;
- the robot is configured, during use, to pierce the pedicle of a vertebra of the patient recumbent on the operating table;
- the robot is configured, during use, to insert a screw into the pedicle of a vertebra of the patient recumbent on the operating table;
- the platform incorporates a presentation area for spinal implants, said presentation area being covered by a field of activity over which the robot is arranged to extend;
- the robot is configured, during use, to assist a surgical act applied by a surgeon to the patient recumbent on the operating table, in particular to guide a drilling tool applied by the surgeon on the pedicle of a vertebra of the patient;
- the uprights are provided with movement and stabilization elements in relation to the ground, these movement and stabilization elements, during use, being designed to alternatively alter the position of the bridge table along the patient recumbent on the operating table by movement on the ground and to immobilize the bridge table in a stable manner on the ground;
- the movement and stabilization elements are casters with brakes;
- one of the uprights incorporates a cabinet inside which an electronic unit is housed, designed to control the robot;
- the bridge table, on an upper face of its platform, integrates at least one surgical instrumentation provisioning area; and
- the bridge table integrates at least one surgical instrumentation provisioning area in at least one of its uprights.

The invention will be better understood upon reading the following description, given only by way of example and made with reference to the drawings in which:

FIGS. 1 to 4 show an installation 1 for performing surgical treatment of the human spine.

Figure 1:
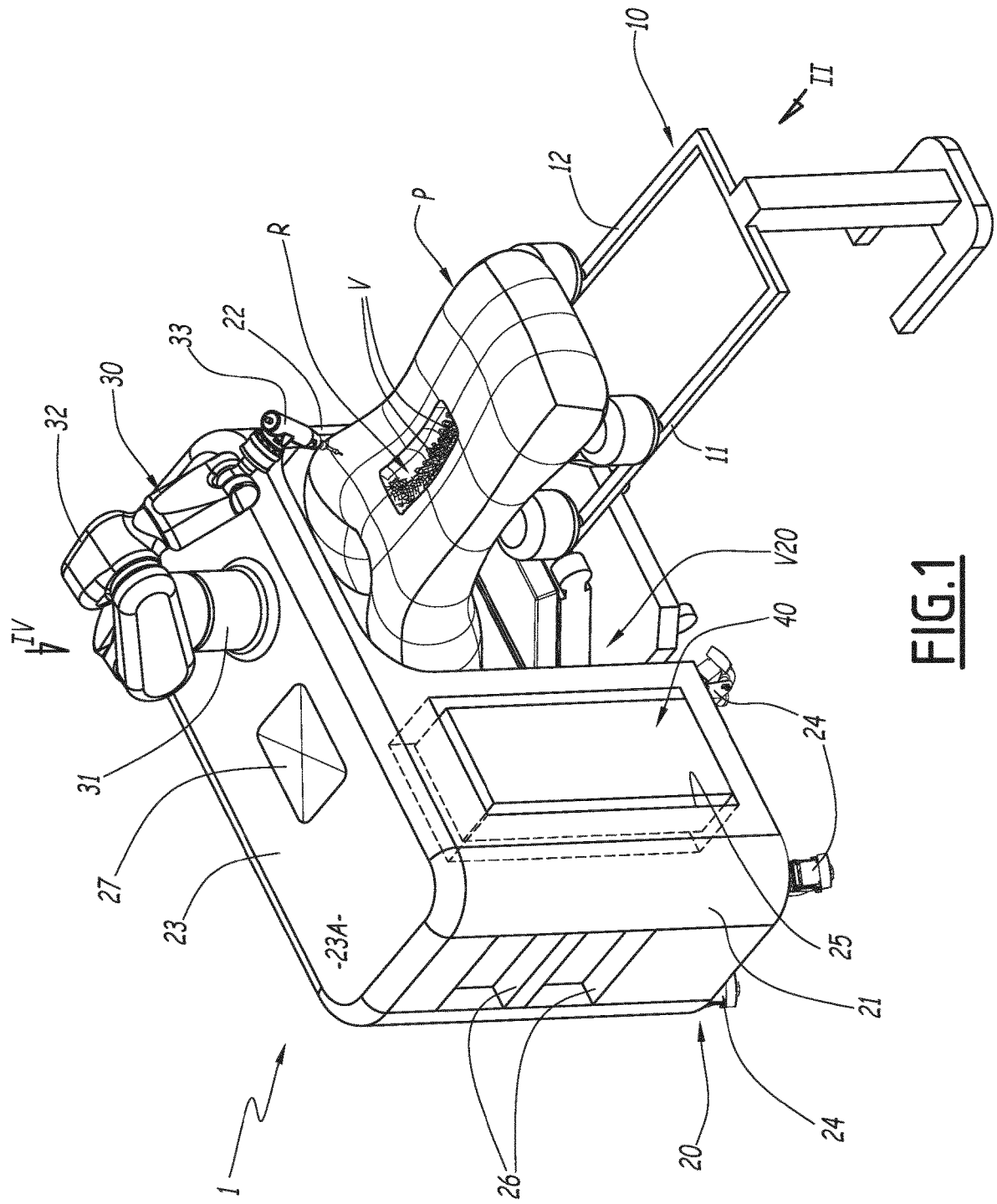
FIG. 1 is a perspective view of a plant in accordance with the invention.
Figure 2:
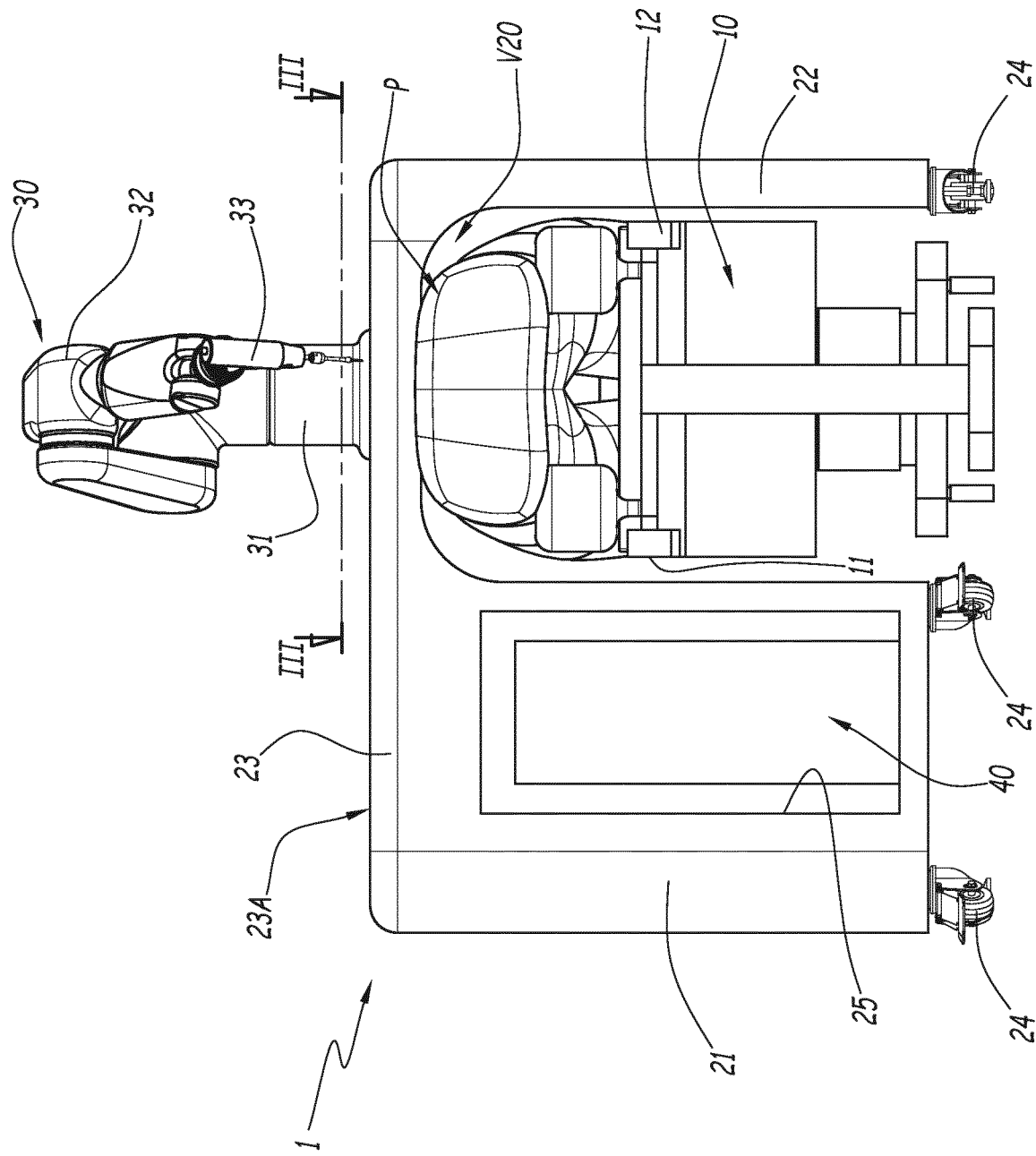
FIG. 2 is an elevation view according to arrow II of FIG. 1.
Figure 3:
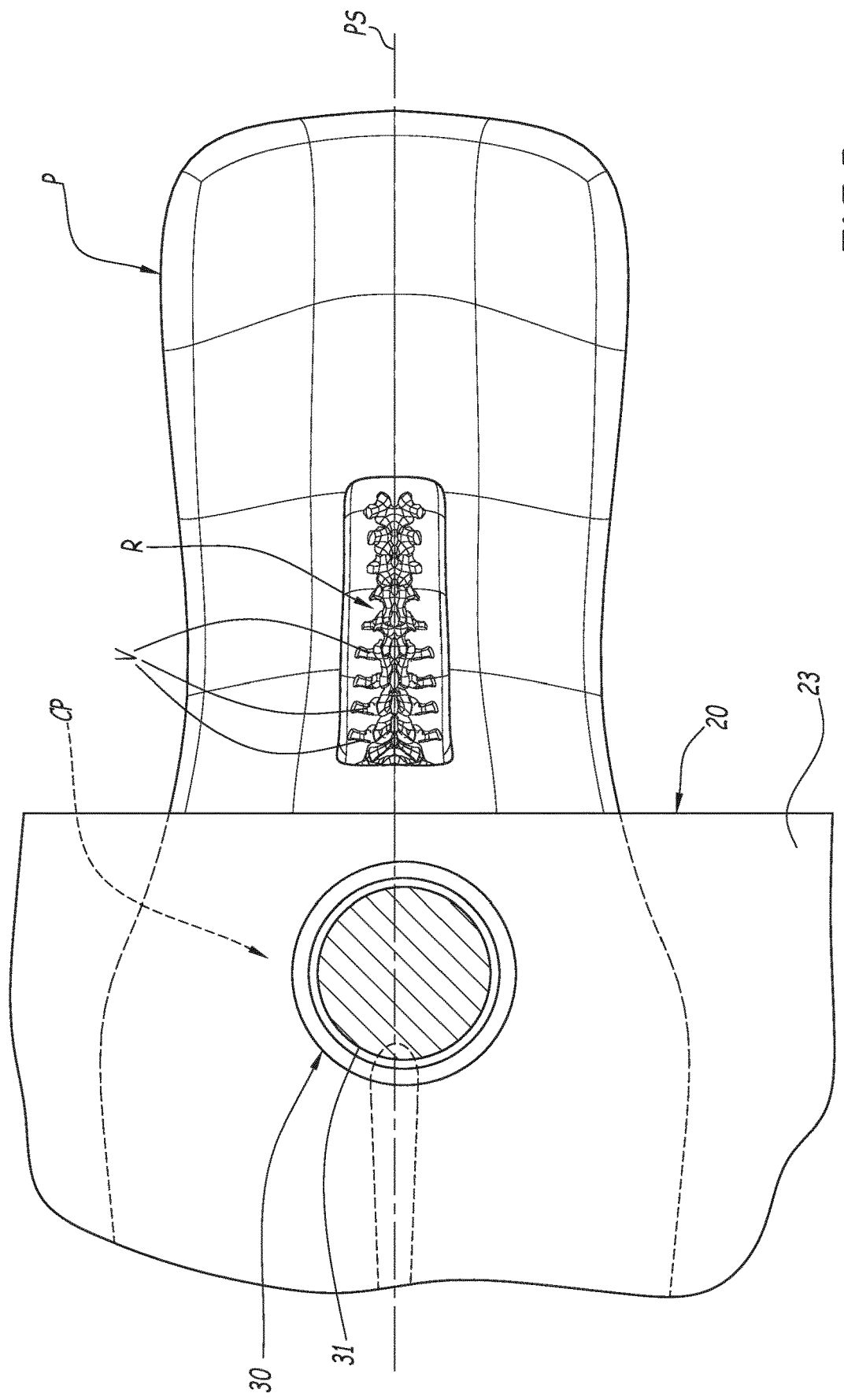
FIG. 3 is a schematic partial section along line III-Ill of FIG. 2.
Figure 4:
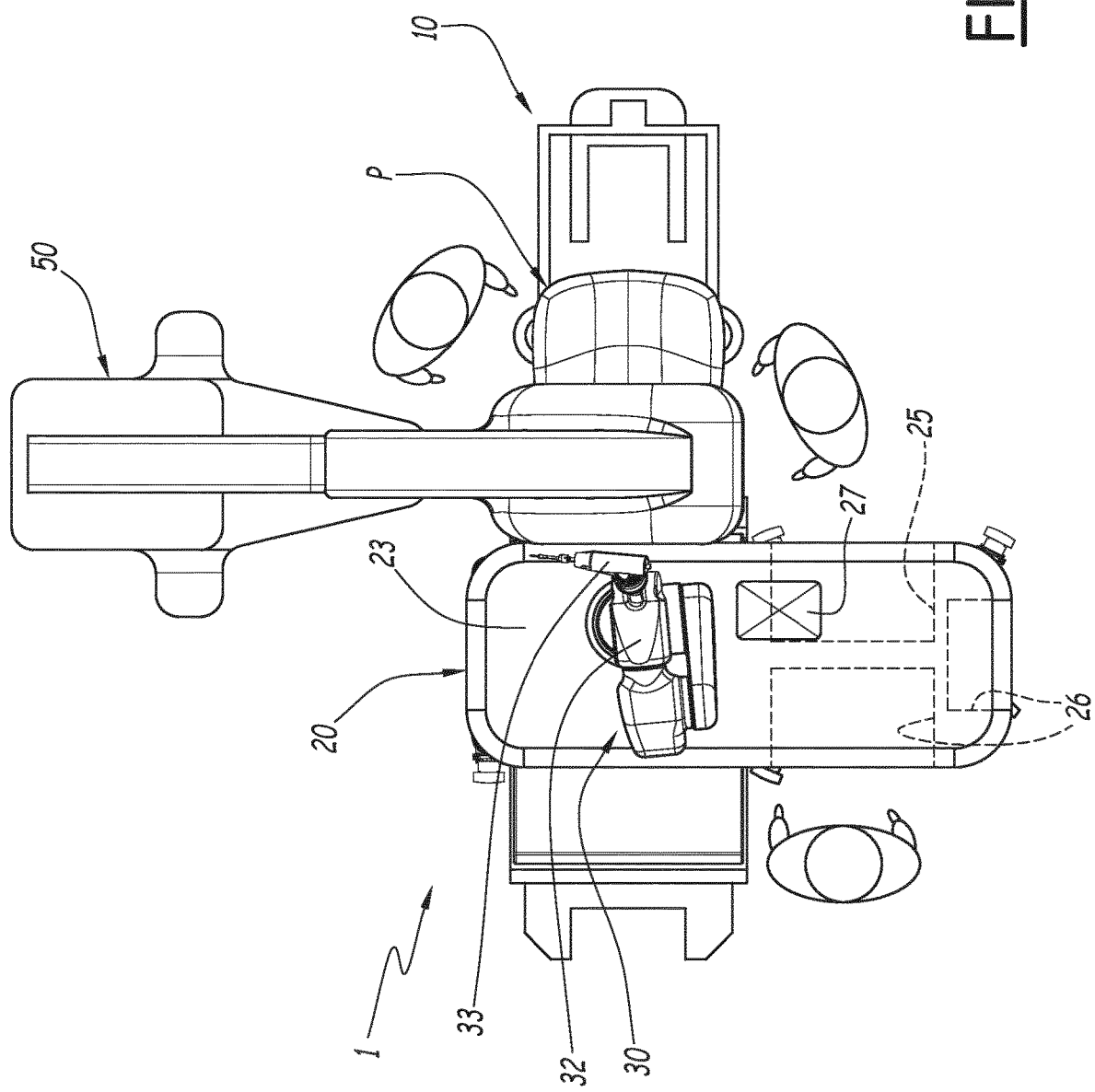
FIG. 4 is an elevation view according to arrow IV of FIG. 1, illustrating the installation during an operating time different from that shown in FIG. 1.

As is clearly visible in FIGS. 1, 2 and 4, the installation 1 includes an operating table 10 on which a patient P to be operated on can be laid. During a surgical procedure using the installation 1, the patient P lies on his or her stomach on the operating table 10: the back of the patient is thus turned upwards and access to the vertebrae V of the patient P is operated from the posterior, as shown schematically in FIGS. 1 and 3. It should be noted that the patient P in the Figures is only drawn schematically and partially, with only the trunk and the upper part of the patient's legs represented.

The embodiment of the operating table 10 is not limitative in the invention, as long as this operating table allows the patient P to lie on his or her stomach. Regardless of the embodiment, the operating table 10 has two opposite lateral sides 11 and 12, which extend on either side of and parallel to the sagittal plane PS of the recumbent patient P.

The installation 1 also includes a bridge table 20 that primarily, if not exclusively, includes uprights 21 and 22 and a platform 23.

The uprights 21 and 22 rise from the ground, generally parallel to each other, being spaced apart so as to form a free space between them. The distance between the uprights 21 and 22 is greater than the distance between the lateral sides 11 and 12 of the operating table 10. The platform 23 rests on the uprights 21 and 22, connecting the respective ends of the uprights 21 and 22, which are opposite to the ground, to each other.

The platform 23 is thus located high above the ground and, upwards, closes a free volume V20 between the uprights 21 and 22. In practice, the platform 23 is located at a sufficient height in relation to the ground so that, when the installation 1 is in use, the platform 23 overhangs the patient P recumbent on the operating table 10 while the latter extends lengthwise through the free volume V20, as clearly visible in the Figures. In other words, when the installation 1 is in use, the uprights 21 and 22 are arranged on either side of the lateral sides 11 and 12 of the operating table 10 and thus rise on either side of the patient P recumbent on the operating table 10, while, at the same time, the platform 23 is located above this patient and extends between the uprights 21 and 22 in a direction that is transverse to the sagittal plane PS of the patient P.

At their base, that is, their end turned towards the ground, the uprights 21 and 22 are advantageously provided with casters with brake 24 enabling, alternatively, moving the bridge table 20 on the ground by rolling the casters and setting a selected position of the bridge table 20 in a stable way along the patient P recumbent on the operating table 10, by action of the brake of the casters. Of course, casters with a brake 24 are only one possible embodiment for movement and stabilization elements in relation to the ground, with which the uprights 21 and 22 are equipped and which, in operation, alternately enable changing the position of the bridge table 20 along the recumbent patient by movement on the ground, by rolling or sliding for example, and then setting the bridge table 20 stably on the ground, by blocking movement for example, or by pressing or even lifting in relation to the ground.

The bridge table 20, in particular its uprights 21 and 22, is separate from the operating table 10, in the sense that no mechanical connection is provided between the bridge table and the operating table.

For reasons that will become apparent later, the upright 21 advantageously has optional arrangements whereby this upright 21 is not identical to the upright 22 but, in particular, has a dimension in the direction along which the platform 24 connects the uprights 21 and 22, that is greater than that of the upright 22. These optional arrangements include a cabinet 25, shown in FIGS. 1 and 2, and one or more niches 26, shown in FIGS. 1 and 4. The cabinet 25 and the niches 26 are integrated into the upright 21, each opening onto at least one of the faces of the upright 21, other than that delimiting the free volume V20.

Also for reasons that will appear later, the platform 23, on its upper face 23A, that is, its face opposite the uprights 21 and 22, integrates a presentation area 27 that is marked by a cross in FIGS. 1 and 4. In the example considered here, this presentation area 27 is at least partly located in line with the upright 21.

The installation 1 also comprises a surgical robot 30. In the example of the embodiment considered here, this robot 30 comprises a foot 31, as well as a robotic arm 32 that extends from the foot 31 and includes successive sections for this purpose, namely a first section carried in a mobile manner by the foot 31, a second section carried in a mobile manner by the first section, and so on. The robot 30 also comprises an effector 33, which terminates the robotic arm 32 opposite the foot 31 and which is carried by the last section of the robotic arm 32. The structure and mobility specifics of the robotic arm 32 are not limiting for the invention: thus, each of the sections of the robotic arm 32 can be mobile in rotation or in translation in relation to the section or the foot 31 carrying it. More generally, the nature of the robot 30 is not limiting as long as this robot is capable of participating in posterior spine surgery.

According to a preferred embodiment, the effector 33 of the robot 30 is designed to perform a surgical act on the patient P, that is, to apply energy that affects the spine R, this energy capable of being of a mechanical, radiative, laser nature, etc. Thus, the effector 33 is then provided to physically act on the spine R, in particular by drilling or cutting the vertebrae and/or by implanting medical devices to be attached therein, in particular by screwing. The effector 33 is designed to pierce the pedicle of the vertebrae V of the patient, for example, P or to introduce a pedicle screw into the vertebral pedicles of the patient. More generally, whatever the specifics of the effector 33, the robot 30 is thus advantageously configured, during use, to perform a surgical procedure on the spine R of the patient P recumbent on the operating table 10.

Whatever its embodiment, the robot 30 is supported by the platform 23 of the bridge table 20, resting on and extending from the upper face 23A of the platform 23, as clearly visible in FIGS. 1 to 4. More precisely, the robot is thus supported by the platform 23 in such a way that its junction with the latter is simultaneously located plumb with the free volume V20, in other words vertically above the free spacing between the uprights 21 and 22, and substantially at the same distance from the uprights 21 and 22 in the direction according to which the platform 24 connects these uprights 21 and 22. When the installation 1 is in use, the robot 30 can thus extend vertically above the spine R of the patient P recumbent on the operating table 10, as illustrated by FIGS. 1 and 2. This arrangement of the robot 30 on the platform 23 allows the robot 30 to be positioned as close as possible to the operated region of the patient P and to extend from the platform 23 both along and vertically above the patient's spine R, being able to align itself substantially in the sagittal plane PS of the recumbent patient: the robot 30 then works in a particularly effective manner, and with the same level of performance on the left and right sides of the spine R, thus adapting to possible pathologies inducing a left-right asymmetry of the vertebrae V.

According to a preferred form of this arrangement, which is implemented in the example considered in the Figures and which is more particularly shown in FIG. 3, the foot 31 of the robot 30 is attached to the platform 23 in such a way that it is substantially centered on the sagittal plane PS of the patient P recumbent on the operating table 10, when the installation 1 is in use. In practice, the attachment of the foot 31 to the platform 23 can be fixed, as in the example embodiment considered in the Figures. However, as an alternative not shown, the foot 31 can be attached to the platform 23 in a mobile manner in order to adjust the relative positioning thereof, this mobility being able to be in translation according to a direction that, during use, is parallel or perpendicular to the sagittal plane PS of the recumbent patient P and/or this mobility being able to be in rotation about an axis perpendicular to the sagittal plane PS of the recumbent patient P.

The robot 30 is advantageously provided to extend over a field of activity, that is covers several vertebrae of the recumbent patient P, in a region of space reachable by its effector 33 by moving its robotic arm 32 relative to the foot 31 and, thereby, relative to the platform 23. Thus, when the installation 1 is in use and the bridge table 20 occupies a fixed position along the patient P recumbent on the operating table 10, the robot 30 has several vertebrae V of the recumbent patient in its field of activity, the robot 30 being thus provided so that its field of activity preferably covers between three and eight vertebrae, in particular five vertebrae. In this way, the effector 33 of the robot 30 can act directly on each of these vertebrae V without having to modify the relative positioning between the bridge table 20 and the recumbent patient P.

In practice, a preferred positioning between the bridge table 20 and the recumbent patient P that results from an appropriate bridge table design and that is implemented in the example shown in the Figures is that the bridge table 20, during use, positions the foot 31 of the robot 30 vertically above the pelvic girdle CP of the patient P recumbent on the operating table 10, this pelvic girdle extending, along the axis of the patient P, from the junction of the sacrum with the patient's lumbar spine, to the patient's hip joint, as clearly visible in FIG. 3. In this way, the robot 30, during use, can intervene effectively and efficiently on the vertebrae that are frequently treated by posterior surgery, namely the sacral vertebrae and the lumbar vertebrae of the recumbent patient P, as well as at least some of the patient's dorsal vertebrae, in particular his last three dorsal vertebrae. Thus, depending on the vertebrae V to be treated for a given patient and depending on the extent of the field of activity of the robot 30, the foot 31 of the robot can remain vertically located above the pelvic girdle CP of the recumbent patient P throughout the duration of using the robot 30 during the surgical procedure, in particular without having to modify the relative positioning between the bridge table 20 and the recumbent patient P. Of course, if necessary, the bridge table 20 can be moved intraoperatively along the recumbent patient P, in particular in the direction of the latter's head, so that the robot's foot 31 can be vertically above the recumbent patient's sacrum and thus remain within the limits of the pelvic girdle CP, or even vertically above the lumbar or even dorsal region of the spine R and thus beyond the recumbent patient's pelvic girdle CP.

Advantageously, the field of activity of the robot 30 also covers the presentation area 27 of the platform 23. In this way, the effector 33 of the robot 30 can reach this presentation area 27 with an appropriate movement of the robotic arm 32, so that by placing spinal implants in this presentation area 27, these implants are presented to the effector 33 so that the latter can pick them up or, more generally, load them from this presentation area 27 before the robot 30 inserts them to the spine R of the recumbent patient P.

The system 1 also includes an electronic unit 40 that is only shown schematically in FIGS. 1 and 2. This electronic unit 40 includes various electronic, electrical and computer components, enabling control if the installation 1. In particular, the electronic unit 40 is designed to control the robot 30: for this purpose, the electronic unit 40 includes a first controller, for example, to control the movement of the robot 30 in relation to the platform 23, in particular to control the movements of the robotic arm 32, and a second controller to control the actuation of the effector 33. The electronic unit 40 may optionally also include a computer running surgical planning software, inter alia. Whatever the material and functional specifics of the electronic unit 40, this electronic unit 40 is advantageously housed inside the cabinet 25 of the bridge table 20, thus optimizing the space requirement and the ergonomics of the installation 1.

Advantageously, the electronic unit 40 is associated with an interface for interacting with a surgeon, this interface being connected to the rest of the electronic unit 40, in particular to the controllers and to the aforementioned computer: thanks to this interface, the surgeon commands and controls the installation 1, in particular the robot 30. In practice, this interface, which is not shown in the Figures, can be supported by the bridge-table 20 at an appropriate height for the surgeon.

During operation of the system 1, the robot 30 is controlled by the surgeon, following instructions entered by the surgeon into the electronic unit 40 via the aforementioned interface. Before the robot 30 carries out the instructions given by the surgeon, the wheels with a brake 24 enable easily adjusting the position of the bridge table 20 and thus of the robot 30 along the patient P recumbent on the operating table 10 and, once this position is reached, setting the latter stably. The robot 30 then carries out the instructions given without its presence or the movements it makes interfering with the surgeon or, more generally, the operating room personnel, thanks to the high position of the robot 30 on the platform 23. As explained above, the operations performed by the robot 30 are carried out in an optimal way, in the sense that the robot extends directly in line with the spine R of the recumbent patient P by adapting if necessary to both left and right asymmetries of this spine R.

During surgery, the layout of the installation 1 allows the robot 30 not to interfere with other materials and equipment in the operating room, as illustrated in FIG. 4. In this FIG. 4, an imager 50, typically an image intensifier, is used on the patient P recumbent on the operating table 10, extending partly above the spine R of the patient P: the bridge table 20 does not interfere with the use of this imager 50 and the robot 30 does not come into contact with the imager 50, moving the robot in relation to the platform 23 if necessary by folding it, as illustrated by FIG. 4. More generally, it is understood that the bridge table 20 and the robot 30 do not interfere with the conventional procedures of surgeons, including the placing and installing other operating materials and equipment used in the proper performance of spinal surgery.

Also during surgery, the surgical instrumentation intended to be handled by hand by the surgeon is advantageously made available in the niches 26 of the bridge table 20 and/or on the upper surface 23A of the platform 23: this surgical instrumentation is placed or stored in the niches 26 and/or on the platform 23, for example, by a nurse in the operating room, before the surgeon can easily take hold of it when he needs it. It is thus understood that the use of ancillary surgical equipment, such as a mobile trolley, can be avoided. Of course, the niches 26 shown in the Figures are only examples of one or more surgical instrumentation provisioning areas, which are advantageously integrated into one and/or the other of the uprights 21 and 22 of the bridge table 20, in addition to one or more other functionally similar areas integrated into the upper surface 23A of the platform 23 of the bridge table.

Furthermore, various arrangements and variants of the installation 1 described so far are conceivable. By way of example:
 rather than the robot 30, during use, being configured to perform a surgical act on the operated patient, this robot can be configured to only assist such a surgical act, the latter being applied by a surgeon on the patient P recumbent on the operating table 10; in this case, the effector 33 is a guide, such as a drilling guide, for example, as discussed in the introductory part of the present document; and/or
 the structure and materials of the bridge table 20 are irrelevant as long as the bridge table 20 can be used in an operating room and supports the robot 30 without risk of breaking or being unstable.

The invention claimed is:
1. An installation for robotic spine surgery, comprising:
 an operating table, which is designed to lay a patient thereon,
 a robot for posterior spine surgery, and
 a bridge table comprising:
  two uprights that are designed to be separated from the operating table when the installation is in use, while being arranged and rising from the ground on either side of the patient recumbent on the operating table, and
  a platform to support the robot, which rests on the uprights so that, during use, the platform lies over the patient recumbent on the operating table and which is designed, during use, to support the robot extending vertically above the spine of the patient recumbent on the operating table,
 wherein the robot is configured, during use, to perform a surgical procedure on the patient recumbent on the operating table, and
 wherein an upper face of the platform includes a presentation area adapted to support a spinal implant, said presentation area being covered by a field of activity over which the robot is configured to extend.
2. The installation according to claim 1, wherein the robot is designed to extend over a field of activity that, when the installation is in use and the bridge table occupies a fixed position alongside the patient recumbent on the operating table, covers several vertebrae of the patient, in particular between three and eight vertebrae of the patient.

3. The installation according to claim 1, wherein the robot comprises:
- a foot that is attached to the platform of the bridge table so as, during use, to be substantially centered on the sagittal plane of the patient recumbent on the operating table, and
- a robotic arm that extends from the foot, being positioned, during use, plumb with the spine of the patient, and which terminates in a spinal surgery effector.

4. The installation according to claim 3, wherein the bridge table is designed, during use, to position the foot of the robot vertically above the pelvic girdle of the patient recumbent on the operating table.

5. The installation according to claim 1, wherein the robot is configured, during use, to pierce the pedicle of a vertebra of the patient recumbent on the operating table.

6. The installation according to claim 1, wherein the robot is configured, during use, to insert a screw into the pedicle of a vertebra of the patient recumbent on the operating table.

7. The installation according to claim 1, wherein the robot is configured, during use, to assist a surgical act applied by a surgeon to the patient recumbent on the operating table.

8. The installation according to claim 1, wherein the uprights are provided with movement and stabilization elements in relation to the ground, these movement and stabilization elements, during use, being designed to alternatively alter the position of the bridge table along the patient recumbent on the operating table by movement on the ground and to immobilize the bridge table in a stable manner on the ground.

9. The installation according to claim 8, wherein the movement and stabilization elements are casters with brakes.

10. The installation according to claim 1, wherein one of the uprights incorporates a cabinet inside which an electronic unit is housed, designed to control the robot.

11. The installation according to claim 1, wherein the bridge table integrates at least one surgical instrumentation provisioning area on an upper face of the platform.

12. The installation according to claim 1, wherein the bridge table integrates at least one surgical instrumentation provisioning area in at least one of its uprights.

* * * * *